(12) United States Patent
Maget et al.

(10) Patent No.: US 9,695,517 B2
(45) Date of Patent: Jul. 4, 2017

(54) TWO-PART, WALL-MOUNTABLE ELECTROCHEMICAL DISPENSER

(71) Applicants: Henri Maget, San Diego, CA (US); Mark Johansson, San Diego, CA (US); James Dikeman, San Diego, CA (US); Randy Houk, San Diego, CA (US)

(72) Inventors: Henri Maget, San Diego, CA (US); Mark Johansson, San Diego, CA (US); James Dikeman, San Diego, CA (US); Randy Houk, San Diego, CA (US)

(73) Assignee: M & R CONSULTING SERVICES, INC., San Diego, CA (US)

( * ) Notice: Subject to any disclaimer, the term of this patent is extended or adjusted under 35 U.S.C. 154(b) by 217 days.

(21) Appl. No.: 14/584,803

(22) Filed: Dec. 29, 2014

(65) Prior Publication Data

US 2016/0184470 A1 Jun. 30, 2016

Related U.S. Application Data

(62) Division of application No. 13/286,690, filed on Dec. 29, 2014, now Pat. No. 8,944,342.

(51) Int. Cl.
*A61L 9/12* (2006.01)
*A61L 9/04* (2006.01)
*C25B 1/04* (2006.01)

(52) U.S. Cl.
CPC ............ *C25B 1/04* (2013.01); *A61L 9/127* (2013.01); *A61L 2209/133* (2013.01); *Y02E 60/366* (2013.01)

(58) Field of Classification Search
CPC ... A61L 9/04; A61L 9/12; A61L 9/122; A61L 9/127; C25B 1/04
See application file for complete search history.

(56) References Cited

U.S. PATENT DOCUMENTS

| | | | |
|---|---|---|---|
| 3,876,115 A | 4/1975 | Venus, Jr. et al. | 222/183 |
| 3,981,415 A | 9/1976 | Fowler et al. | 222/95 |
| 4,341,348 A | 7/1982 | Dearling | 239/34 |
| 4,776,499 A | 10/1988 | Magid | 222/386.5 |
| 4,902,278 A | 2/1990 | Maget et al. | 604/132 |
| 5,090,963 A * | 2/1992 | Gross | A61M 5/155 128/DIG. 12 |
| 5,242,565 A | 9/1993 | Winsel | 204/265 |

(Continued)

*Primary Examiner* — Darren W Gorman
(74) *Attorney, Agent, or Firm* — Steins & Associates, P.C.

(57) ABSTRACT

A Two-part, Wall-mountable Electrochemical Dispenser. The dispenser assembly consists of a disposable fluid storage reservoir and a non-disposable dispenser. The dispenser holds an electrochemical gas generator, its associated electronics, and a power source. The generator can be set for fluid delivery rates of between 1 mL/day and 50 mL/day. The system has a battery-determined operational life of about 2 years, assuming rates of up to 2 mL/day and 2 C-size batteries. The fluid storage reservoir is formed by two plastic shells separated by a plastic diaphragm. Gas produced by the generator acts on the diaphragm thereby displacing fluid that is then captured by an evaporation pad from which it can readily emanate into the environment. The reservoir can be removed and discarded after depletion of the liquid, and then replaced by another filled assembly. As needed, the refill holds an anti-theft coded card that prohibits the re-use of the refill.

10 Claims, 15 Drawing Sheets

(56) References Cited

U.S. PATENT DOCUMENTS

| | | | | |
|---|---|---|---|---|
| 5,427,870 | A | 6/1995 | Joshi et al. | 429/27 |
| 5,445,462 | A | 8/1995 | Johnson et al. | 401/132 |
| 5,681,435 | A | 10/1997 | Joshi et al. | 204/266 |
| 5,785,688 | A | 7/1998 | Joshi et al. | 604/141 |
| 5,899,381 | A | 5/1999 | Gordon et al. | 239/6 |
| 5,928,194 | A | 7/1999 | Maget | 604/141 |
| 5,932,204 | A | 8/1999 | Joshi | 424/76.1 |
| 5,938,640 | A | 8/1999 | Maget et al. | 604/145 |
| 5,997,501 | A * | 12/1999 | Gross | A61M 5/14248 604/65 |
| 6,042,704 | A * | 3/2000 | Joshi | A61M 5/145 204/265 |
| 6,383,165 | B1 | 5/2002 | Maget et al. | 604/141 |
| 6,413,238 | B1 | 7/2002 | Maget | 604/132 |
| 6,451,808 | B1 | 9/2002 | Cowles | 514/290 |
| 7,681,809 | B2 | 3/2010 | Maget et al. | 239/326 |

* cited by examiner

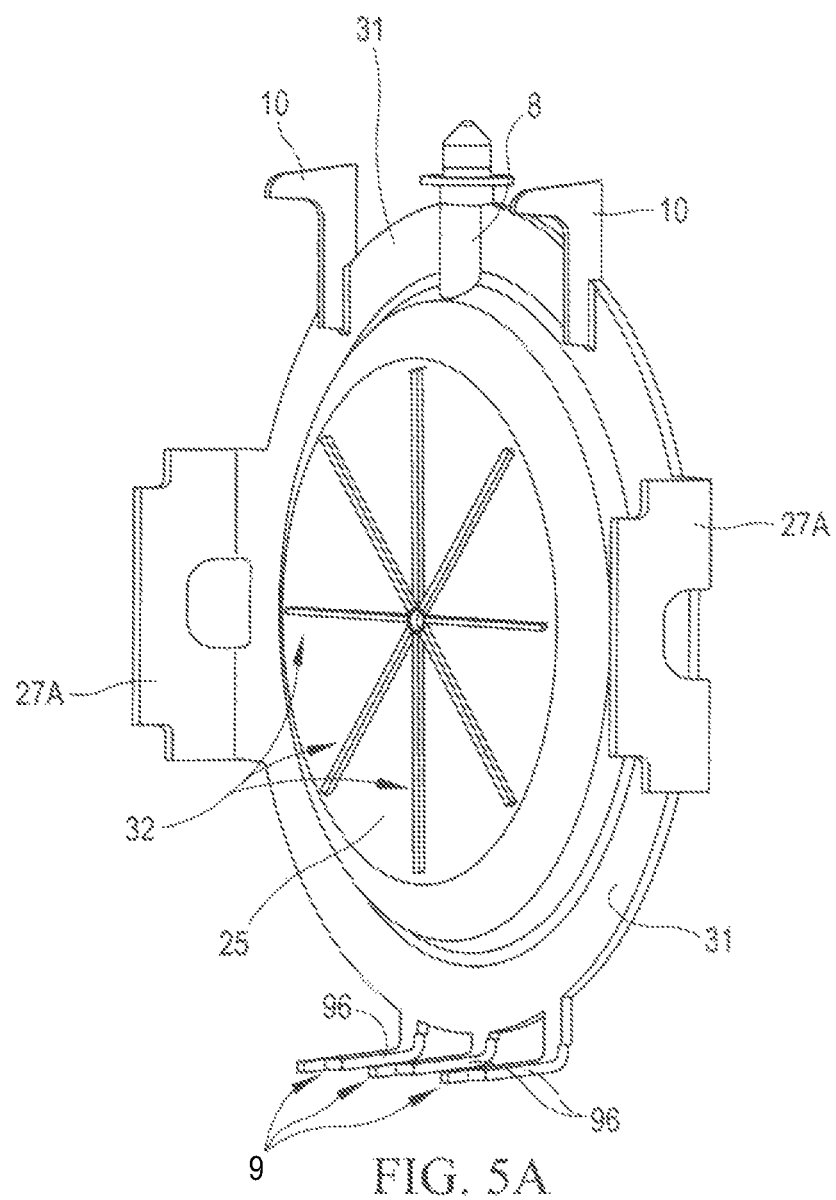

TWO-PART, WALL-MOUNTABLE ELECTROCHEMICAL DISPENSER

This application is a Divisional Continuing Application of application Ser. No. 13/286,690, filed 11 Jan. 2011; status: Now Pending.

BACKGROUND OF THE INVENTION

1. Field of the Invention

This invention relates generally to vapor release dispensing devices and, more specifically, to a Two-part, Wall-mountable Electrochemical Dispenser.

2. Description of Related Art

In recent years, numerous devices and systems have been developed to treat the environmental air scent in public, institutional areas. The alteration of the environmental air in restrooms, hospitals, hotel lobbies, etc. has been achieved predominantly through the use of low-emission-rate fragrance dispensers. In order to serve the institutional market, these fragrance dispensers must not only provide low rate, long term fragrance emission, but must do so economically.

Dr. Henri Maget, alone and in cooperation with other inventors, has developed various such fluid releasers, as described in previous U.S. Pat. No. 4,902,278 (Maget I), U.S. Pat. No. 5,928,194 (Maget II), U.S. Pat. No. 6,383,165 (Maget IV), and U.S. Pat. No. 7,681,809 (Maget V). These patents disclose devices that release fragrances, pheromones or other such chemicals and mixtures at low rates (generally less than 1 mL of fluid per day). Other inventors have also developed dispensers as described in U.S. Pat. No. 5,899,381 (Gordon, et al), U.S. Pat. No. 6,451,808 (Cowles); and U.S. Pat. No. 5,785,688 (Joshi, et al), for example.

Often these active dispensers made use of a gas source to control the release rates of the dispensed fluid (and therefore also the emanation rates). Miniature gas sources, based on electrochemical reactions, have been described by Maget V. In general, for cost reasons, the electronic control of the gas generators in these active dispensers is accomplished by means of a simple, low-cost resistor. Also, in most instances, the electrochemical gas source is integrated into the dispenser. Problems have arisen whenever more complex delivery modes (e.g. variable fluid flow rates) or control functions (e.g. timers, end-of-delivery detection, etc.) are needed. The increased cost resulting from the cost of the electronics components, batteries, and the gas generator are not compatible with a single use dispenser. Consequently, it becomes desirable to split the delivery system into two subsystems—one permanent (or semi-permanent), and one disposable/consumable. The (semi)permanent subsystem preferably includes the gas generator and its related electronics, while the disposable subsystem generally consists of the fluid refill.

Two-part dispensers offer the advantage of multiple uses, so that the cost of the dispenser can be amortized over all of the uses (rather than a single use). These two-part dispensers couple economical refills that are replaceable once per month or so, with a (semi)permanent dispenser, replaceable once every 2-3 years or so. Such a dispenser is described by Maget, et al in U.S. Pat. No. 5,938,640 (Maget III). The battery-operated gas generation sub-assembly of Maget III is detachable from the fluid reservoir. Fluid delivery is achieved by the application of gas pressure to a membrane within the fluid chamber. The fluid reservoir is disposable, while the gas generation sub-assembly is re-usable.

SUMMARY OF THE INVENTION

In light of the aforementioned problems associated with the prior devices, it is an object of the present invention to provide a Two-part, Wall-mountable Electrochemical Dispenser. The dispenser should incorporate an improved interface between the disposable fluid reservoir and the semi-permanent gas generator. The dispenser should provide a variety of high-level electronic features, including digital current selection, visible on/off indication, end-of-delivery signal, system shut-off, and even including protection from unauthorized use by non-qualified individuals. The dispenser should be wall-mountable. A dispenser pad should be implemented in order to permit the dispensed fluid to evaporate gradually and evenly. The protection from unauthorized use is preferably implemented by use of a low-cost, simple coded circuit board incorporated in the fluid refill subsystem. Unless the refill circuit board provides the proper status to the dispenser circuitry when the refill is mated with the dispenser, the dispenser should not operate. Finally, the refill subsystem should incorporate a mechanically-sealed fluid dispense port that must be physically removed before the dispenser can be started up. In order to provide visible indication of dispenser readiness (or lack thereof), failure to properly remove the fluid dispense port protection element should prevent the lid from being closed in the housing.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings, of which:

FIGS. 5A and 5B are perspective views of the liquid- and gas-side shells of the module assembly of FIG. 4;

DETAILED DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the generic principles of the present invention have been defined herein specifically to provide a Two-part, Wall-mountable Electrochemical Dispenser.

Figure 1:
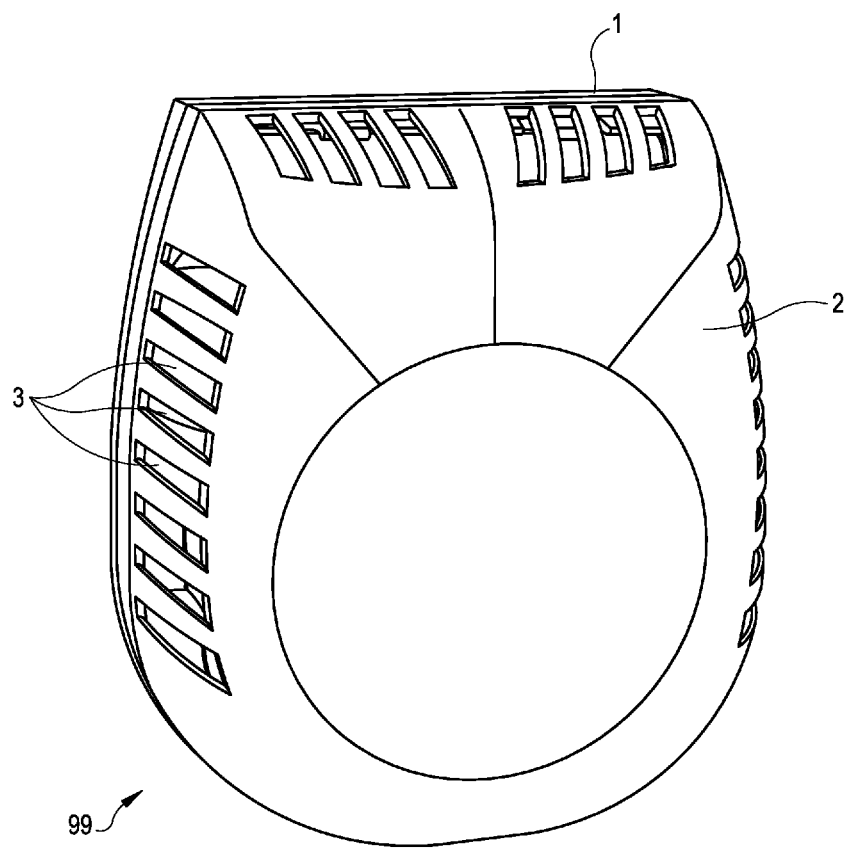
FIG. 1 is a front perspective view of a preferred embodiment of the two-part, wall-mountable electrochemical dispenser assembly of the present invention.

The present invention can best be understood by initial consideration of FIG. 1. FIG. 1 is a front perspective view of a preferred embodiment of the two-part, wall-mountable electrochemical dispenser assembly 99 of the present invention. The assembly 99 consists of a base plate 1, which is the mounting location for all of the functional components of the assembly 99. A slotted lid 2 removably attaches (e.g. snaps) to the base plate 1. Air slots 3 are required to allow air flow over the evaporation pad to be described in the following. Removing the lid 2 exposes the visible frontal components of the dispenser assembly 99.

Figure 2:
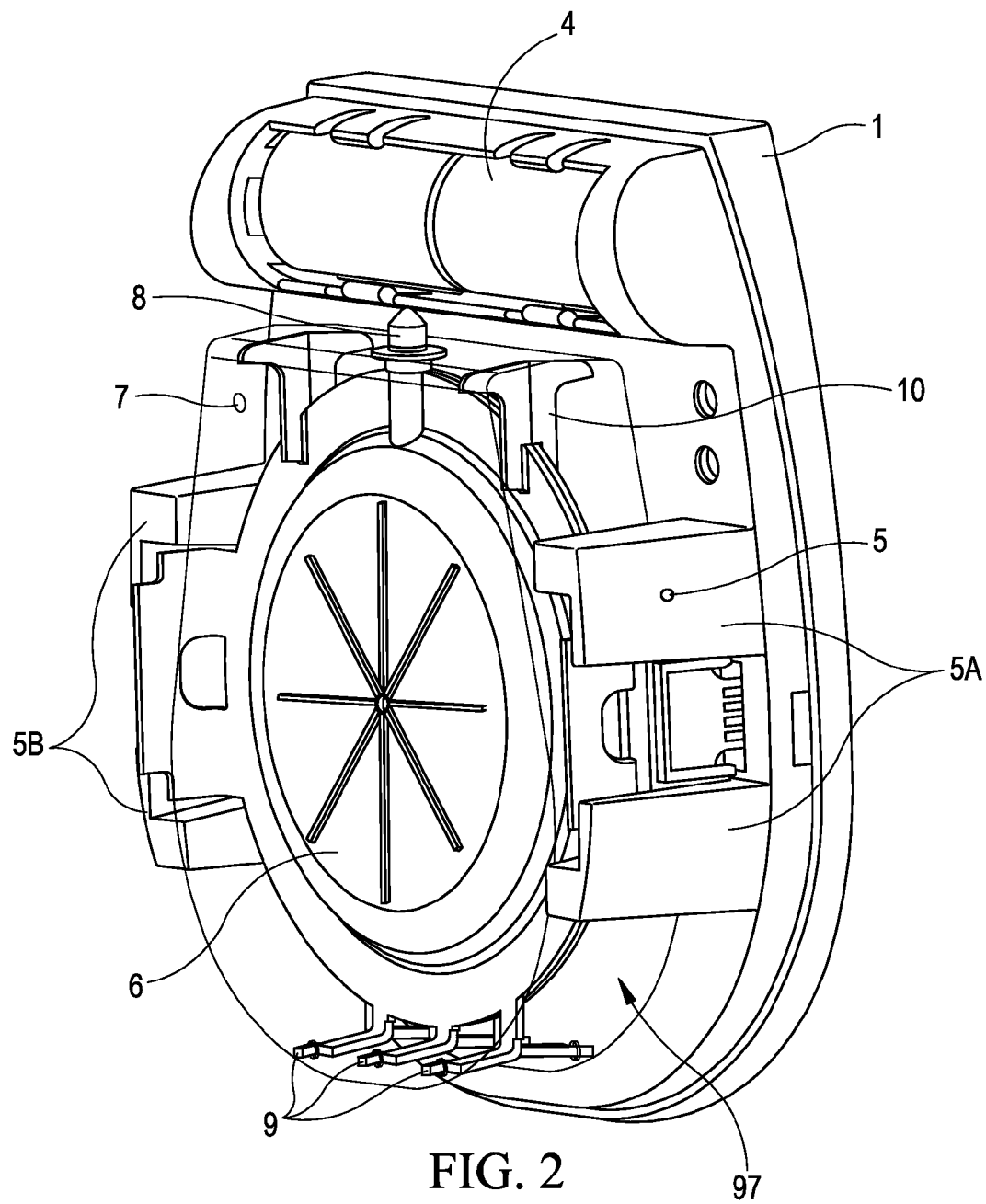
FIG. 2 is a perspective view of the assembly of FIG. 1, having its lid removed.

FIG. 2 is a perspective view of the assembly 99 of FIG. 1, having its lid removed. The base plate 1 holds two alkaline C-size batteries 4 and four guide elements 5 extending upwardly therefrom. The guide elements 5A and 5B are needed to assist the user in inserting the refill module assembly (see FIG. 4) into its exact location on the base plate 1. A plurality of pad shoulder elements 10 extend from the refill module assembly 97, over which the evaporation pad 7 is stretched. The pad 7 is held in this stretched condition by a plurality of pad retention prongs 9 extending outwardly from the bottom end of the refill module assembly 97. The reservoir 6 of the module assembly 97 is filled by feeding the dispensable liquid into the fluid fill nozzle 8. Further detail regarding each of these subsystems and modules is provided herein below in connection with subsequent drawing figures.

Figure 3A:
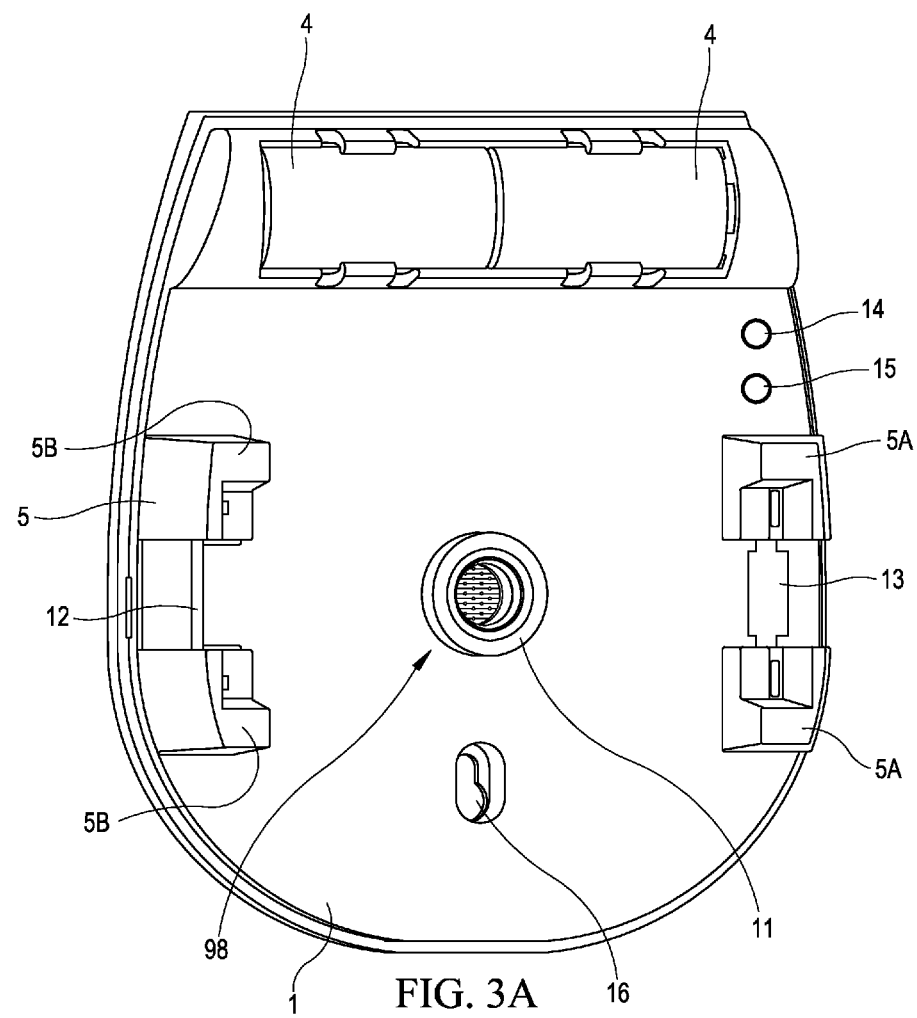
FIGS. 3A and 3B are front and rear perspective views, respectively, of the assembly of FIGS. 1 and 2 having the lid and refill module removed.
Figure 3B:
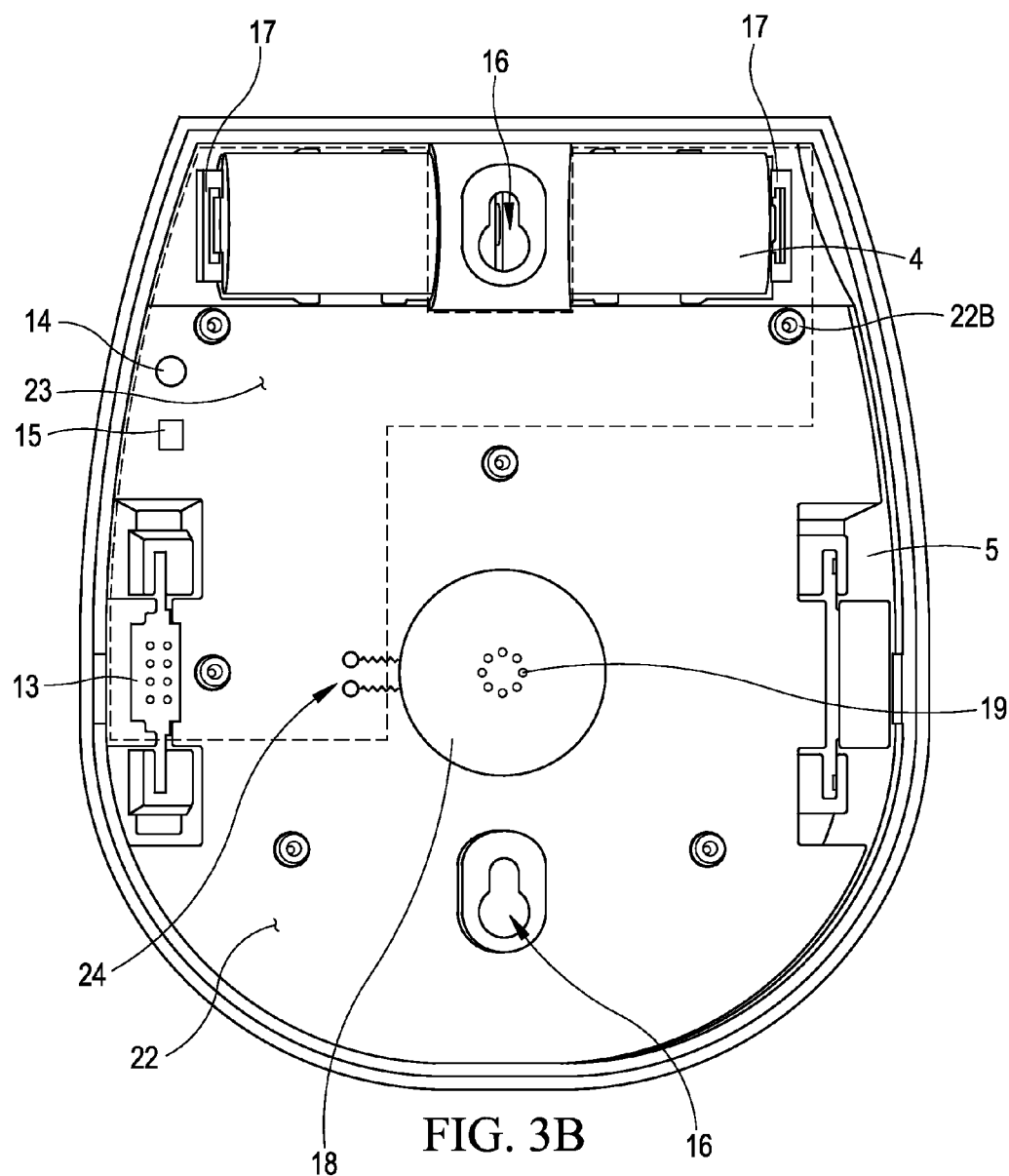

FIGS. 3A and 3B are front and rear perspective views, respectively, of the assembly of FIGS. 1 and 2 having the lid and refill module removed. This view depicts the dispenser assembly base plate 1, prior to installation of the refill, and shows the features of that plate 1, namely four refill guides 5A/5B, a port 11 within which the gas generator module assembly 98 is received and retained. A pair of slots 12 to receive the wings (27A, 27B, 28) are provided, one of which is configured to hold the key connector 13. There are ports formed in the plate 1 to receive an LED 14 and a switch 15, and further 2 apertures 16 for mounting of the base plate 1 onto a vertical surface, such as a wall or the like.

The rear perspective view of the base plate 1 shows the batteries 4 with a pair of battery contact clips 17 providing electrical connection thereto. Further shown is the main printed circuit board 23 (absent component details), mounted to which are the LED 14, switch 15 and key connector 13. The electrochemical cell module (ECM) or gas generator 18 with its air intake ports 19 is mounted rigidly onto the base plate, with its leads 24 (cathode and anode) being connected to the PCB 23. Six base plate assembly studs 22 are provided, 3 of which are used to rigidly attach the PCB 23 to the back plate, with the others being provided to mount a protective cover plate (not shown) against the base plate 1. Wiring between gas generator 18 and batteries is achieved by means of the PCB 23. FIGS. 4 through 7B provide technical detail related to the refill module assembly and associated elements.

Figure 4:
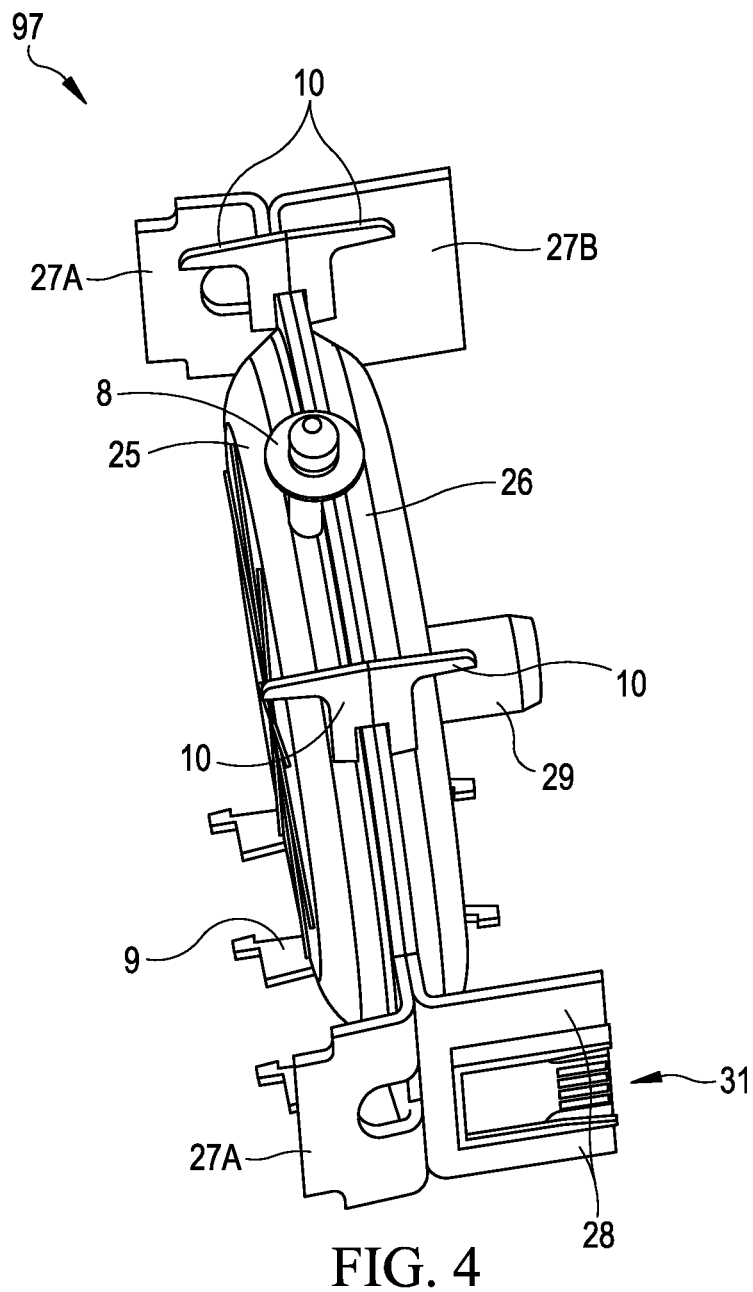
FIG. 4 is a side view of a preferred embodiment of a refill module assembly of the assembly of FIGS. 1-3.

FIG. 4 is a side view of a preferred embodiment of a refill module assembly 97 of the dispenser assembly of FIGS. 1-3. The refill module assembly 97 consists of the a pair of plastic (Barex, PE, etc.) shells 25, 26 that form fluid reservoir 6 along with diaphragm (not shown), disposable evaporation pad (not shown), fluid exit nozzle 8 and prongs 9 needed to hold pad 7 in place. The assembled refill has two vertical shoulder elements 10 that allow evaporation pad 7 to wrap-around the reservoir without directly resting upon it. Component materials are selected using criteria of chemical compatibility with fluids to be released (i.e. fragrances, etc.) and low oxygen transmission rates. Specifically, the liquid-side shell 25 needs to be stable and non-reactive to fragrances and other chemicals over long time periods. The gas-side shell 26 needs to have a high resistance to oxygen diffusion, in order to avoid variability (or loss of control) in the liquid release rate. Finally, the separating diaphragm (not shown—see FIG. 6) has to satisfy both of these requirements, namely chemical stability and low oxygen permeability, in addition to being reasonably flexible, so that it permits an acceptable amount of lateral displacement. It has been determined that Barex films of about 100 microns thickness are compatible with these requirements.

Figure 5B:
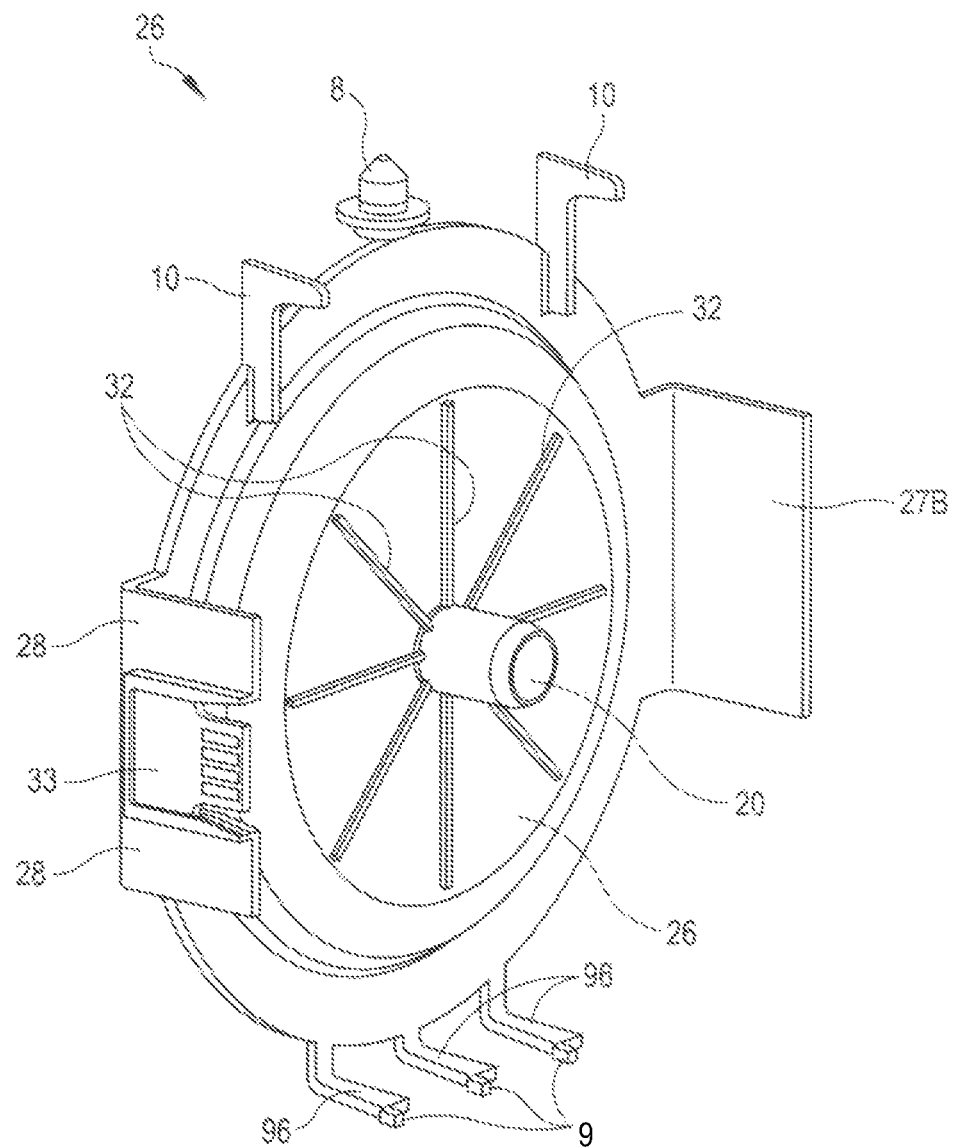

The nipple 29 provides a conduit through which oxygen generated by the Electrochemical Cell is transported into the interior of the gas-side shell 26. The wings 27A, 27B and 28 cooperate with the slots (12—see FIG. 3A) and guide elements (5A, 5B—see FIG. 3A) to guide the refill assembly 97 to engage the base plate 1 properly. FIGS. 5A and 5B are provided in order to support the exploration of the features of the individual shells comprising the module assembly 97.

FIGS. 5A and 5B are perspective views of the liquid- and gas-side shells of the module assembly of FIG. 4. The shells 25 and 26 are not symmetrical. The liquid-side shell 25 (FIG. 5A) has two (2) wings 27A located vertically and extending outwardly from the surface of the shell 25. These wings 27A are used to hold the refill assembly in a controlled position while inserting the refill assembly into the base plate (i.e. along the guide elements).

The shoulder elements 10 (two (2) on each shell) provide a saddle for the fluid capture pad 7 (see FIGS. 7A and 7B) once the shells are assembled. Six (6) prongs 9, three (3) on each shell, protrude from the distal ends of the fingers 96 extending from the shell 25 (and 26) are used to hold the pad 7 in a location in spaced relation from the shell (25, 26) surfaces. The liquid fill/exit port 8 is used to supply to, and to remove liquid from the refill assembly.

The flange 31 (one flange on each shell) is designed to allow for the mating of the shells as well as entrapping the diaphragm (see FIG. 6) therebetween. Stiffening members 32 are provided on each shell to minimize shell flexing during dispenser operation.

The refill gas-side shell 26 (FIG. 5B) has three features that differentiate it from the liquid-side shell. This shell 26 does not require any liquid input/exit ports; the modified wing 28 is configured to hold a small printed circuit board (the electronic key device 33) within it. The electronic key device is provided with four (4) contact pads 40. The final distinction between this shell 26 and the liquid-side shell is the nipple 29. As discussed previously, the nipple 29 interfaces with the gas generator when the refill is mated with the base plate to allow the gas generated by the gas generator to enter into the internal chamber of the gas-side shell 26. The other wing 27B is essentially the modified wing 28, but without the provision for holding the key device 33 within it. If we turn to FIG. 6, we can examine how the two shells and diaphragm are assembled to form the base of the refill module assembly.

Figure 6:
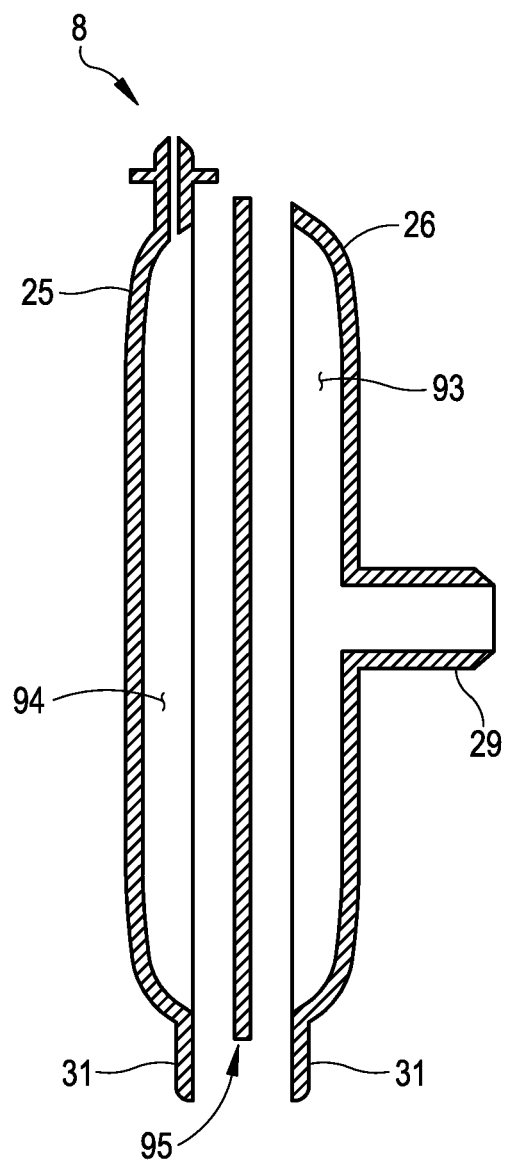
FIG. 6 is a partially exploded cutaway view of the module of FIG. 4.

FIG. 6 is a partially exploded cutaway view of the module of FIG. 4. The diaphragm 95 is captured between the flanges 31 formed around the perimeter of each shell 25, 26 when the shells are bonded to one another. The diaphragm 95 is pre-formed to match the internal surface geometry of the gas-side shell 26 (i.e. it is curved to fit the internal curve of the gas-side shell 26) to minimize the dead-space between diaphragm and shell 26, thereby allowing diaphragm 95 lateral displacement as soon as the gas generator begins generating gas (that reaches the gas-side shell 26 via the gas inlet nipple 29).

The diaphragm 95 seals to, and separates the liquid chamber 94 from the gas chamber 93. Liquid is retained within the liquid chamber 94 until sufficient pressure is exerted on the chamber 94 by the diaphragm 95. As gas pressure increases in the gas chamber 93, liquid will be forced out through fluid exit port at the top of the assembly. As liquid is forced out of the liquid chamber 94, it will be absorbed into the pad (7, see FIGS. 7A and 7B), where it will be gradually released by evaporation into the surrounding environment.

Figure 7A:
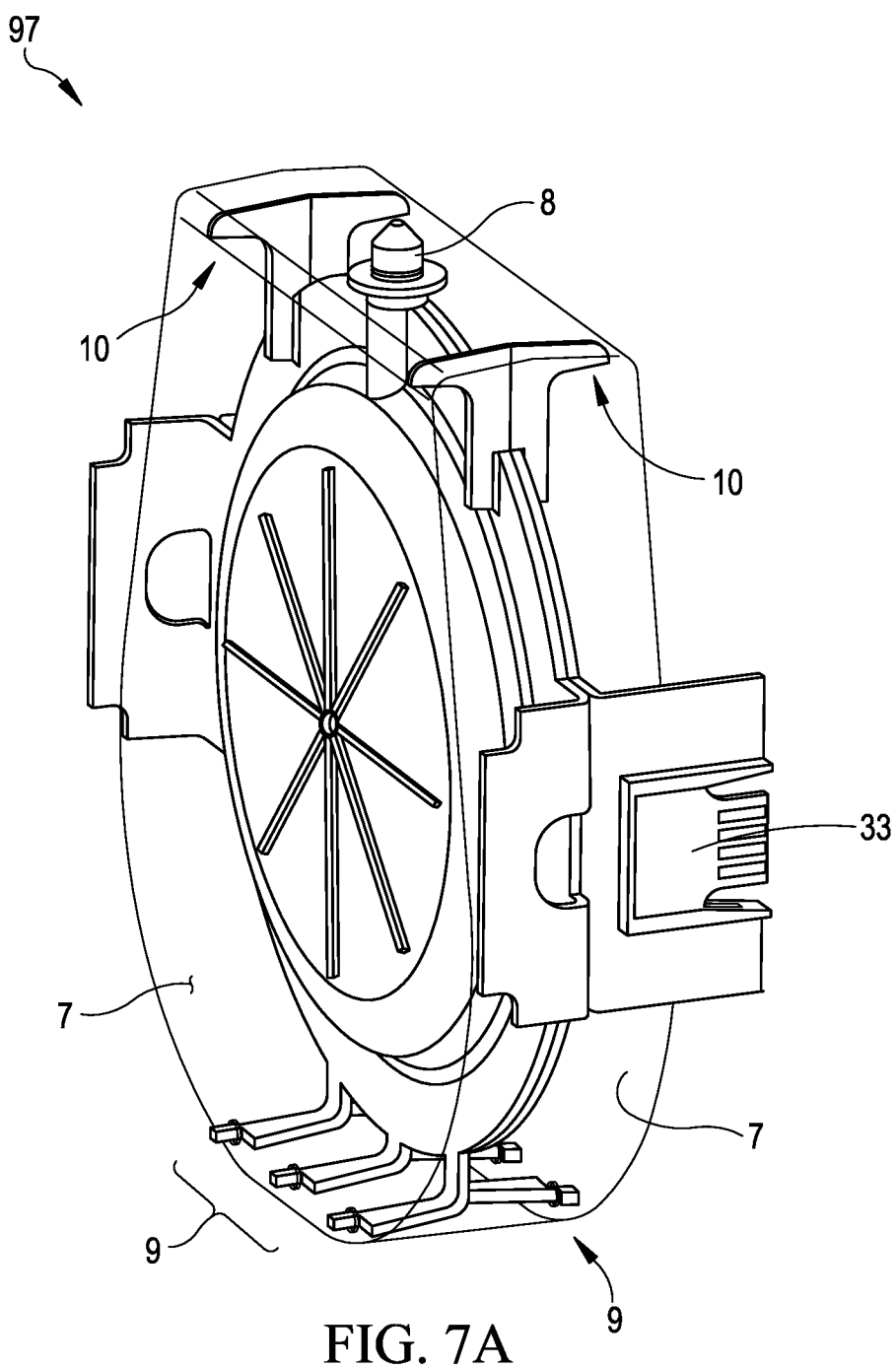
FIGS. 7A and 7B are front and rear perspective views of the module of FIGS. 4 and 6 having a preferred embodiment of the pad installed thereon.
Figure 7B:
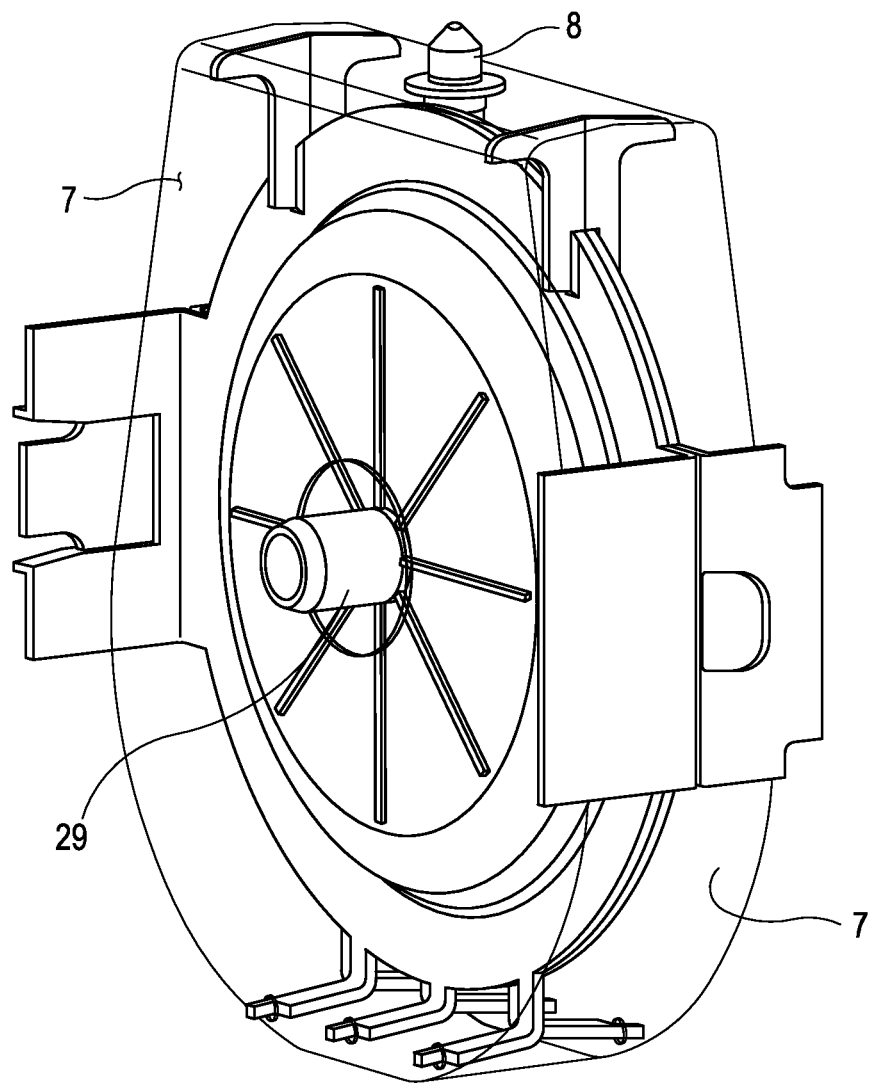
Figure 8A:
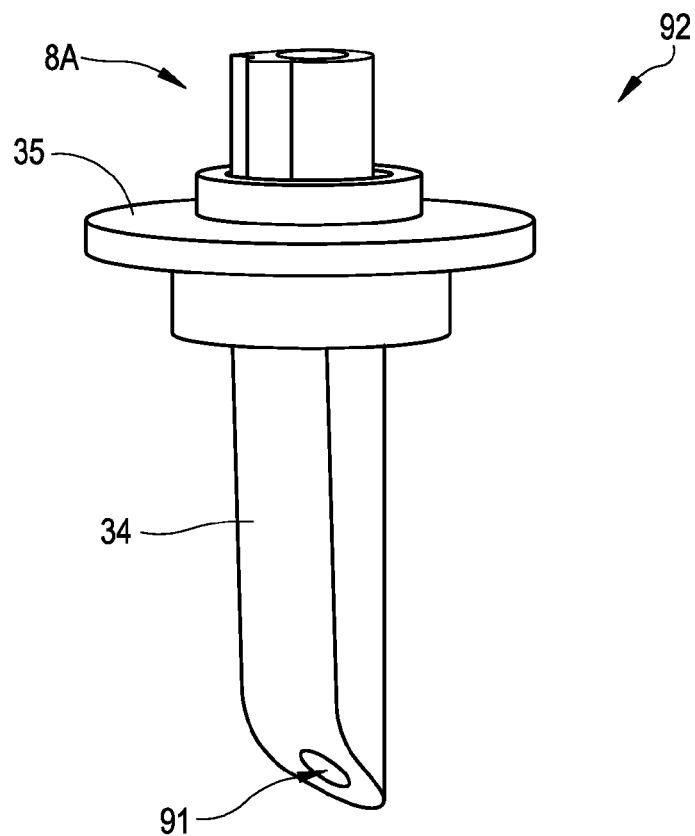
FIGS. 8A and 8B are side and top views, respectively, of a preferred embodiment of a fill port element of the module of FIGS. 4, 6 and 7A/7B.
Figure 8B:
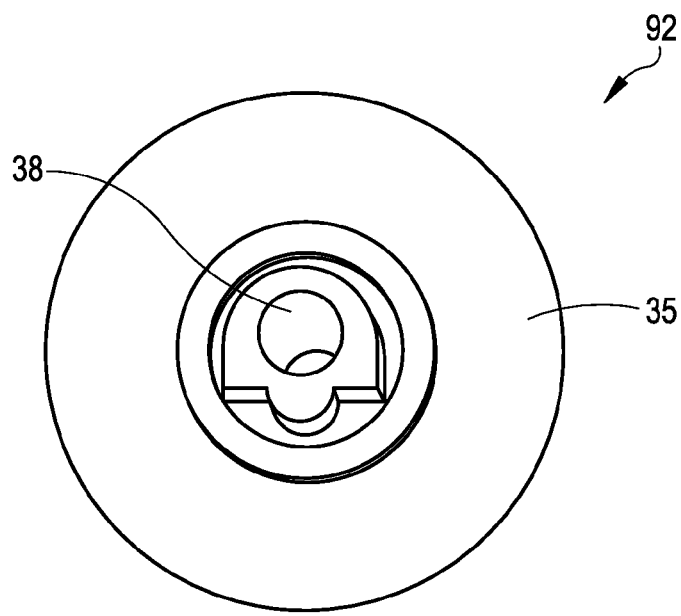
Figure 9A:
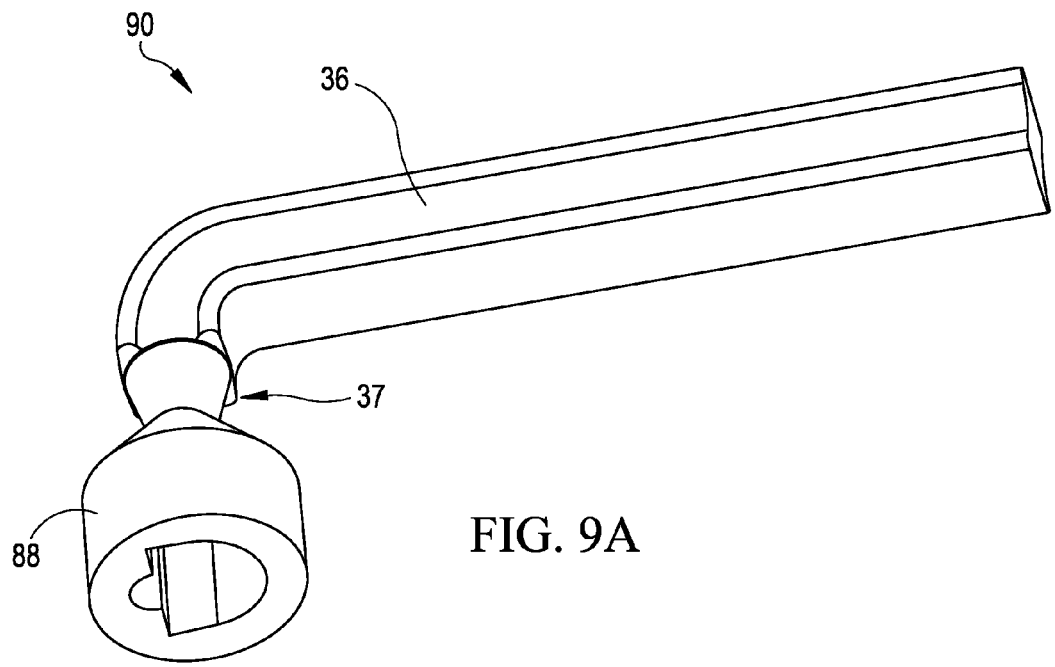
FIGS. 9A and 9B are perspective and back views, respectively, of a preferred embodiment of the break-away arm element of the present invention.
Figure 9B:
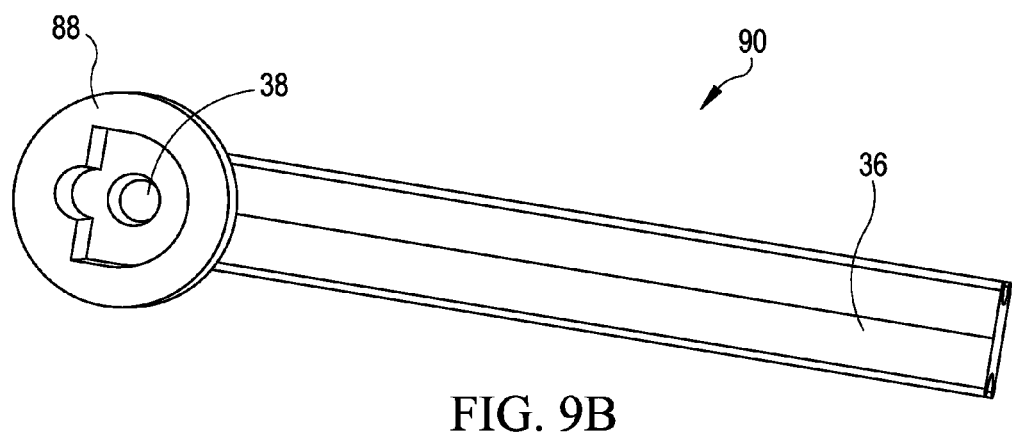

FIGS. 7A and 7B are front and rear perspective views of the module assembly 97 of FIGS. 4 and 6 having a preferred embodiment of the pad 7 installed thereon. As discussed above, liquid is emitted from the face of permeation wall 92 of the liquid-side shell. The pad 7 extends between the prongs 9 extending from the gas-side shell and the prongs 9 extending from the liquid-side shell, so that it is held away from the outer surfaces of the shells 25, 26.

FIGS. 8A, 8B, 9A and 9B describe the structure and functionality of the fill port element 92 and break-away arm element 90. Fluid fill/exit port 8 consists of a fill port spike 34, that is inserted and bonded to liquid-side shell 25. The wide port 8 is used to fill the reservoir liquid-side (once the two shells and diaphragm have been bonded or ultrasonically welded together). Once filled, the fluid port break-away arm element 90 (FIGS. 9A, 9B) is bonded to the fill port flange 35. The arm 90 has a break-away surface 37 that, whenever snapped-away from the refill, reveals a fluid exit opening 38 that is substantially smaller than fill port 8. Once the arm 36 is broken away from the head portion 88 of the arm element 90, the fluid exit opening 38 becomes the fluid release port. The fluid is dispensed through this opening 38 such that it drips onto the evaporation pad for evaporation into the environment.

Figure 10A:
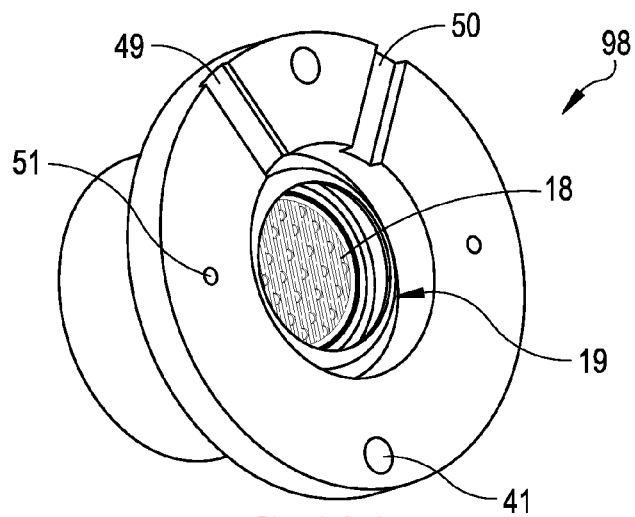
FIGS. 10A, 10B and 10C are front perspective, rear perspective and cutaway side views, respectively, of the gas generator module assembly of the refill module of FIGS. 4, 6, 7A/7B and 8A/8B.
Figure 10B:
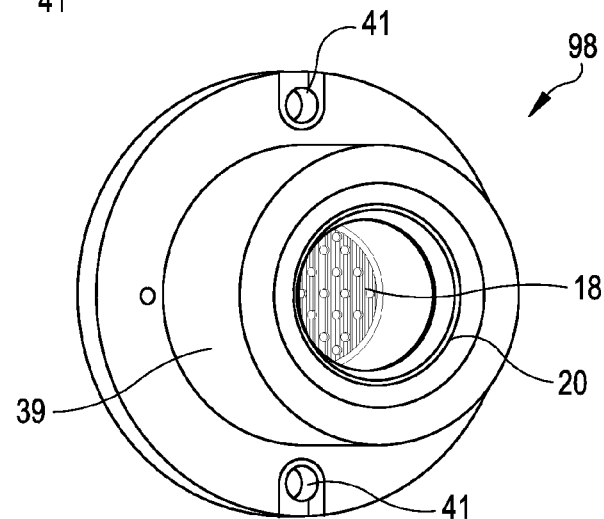
Figure 10C:
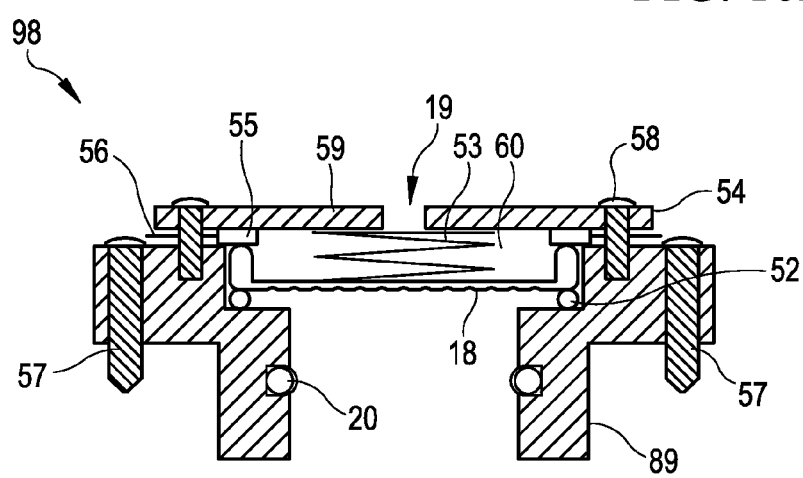

FIGS. 10A, 10B and 10C are front perspective, rear perspective and cutaway side views, respectively, of the gas generator module assembly 98 of the refill module of FIGS. 4, 6, 7A/7B and 8A/8B. The assembly 98 houses the reusable electrochemical cell (ECM) 18, which has previously been described by Maget et al in U.S. Pat. No. 6,010,317. The ECM 18 is installed in a module cavity 60 formed in the ECM module housing 89, so as to rest on seal 52.

Reliable electrical contact with the ECM cathode is achieved by spring 53 with a lead wire 54 exiting through channel 50. Anode contact is achieved by means of washer 55 attached to lead wire 56 exiting through channel 49. A compression plate 59 applies a load to the spring 53 and washer 55 when the plate 59 is attached to module sleeve 39 by means of two screws 58. Similarly, module sleeve 39 is rigidly held in place by means of screws 57, which join the sleeve 39 to base plate 1. This arrangement facilitates the replacement of the gas generator module 18, if need be. The internal diameter of module sleeve 39, including seal 40 (now part of base plate 1) is designed to mate with nipple 29 of the refill in an airtight manner.

Figure 11A:
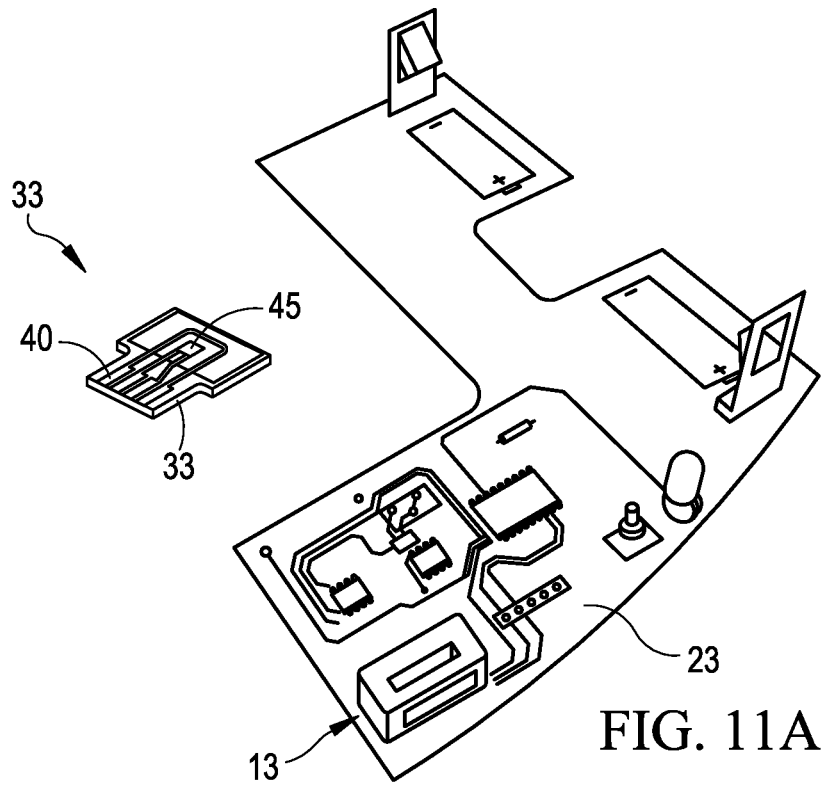
FIGS. 11A and 11B are perspective views of the main circuit board and electronic key device of the assembly of FIGS. 1-4.
Figure 11B:
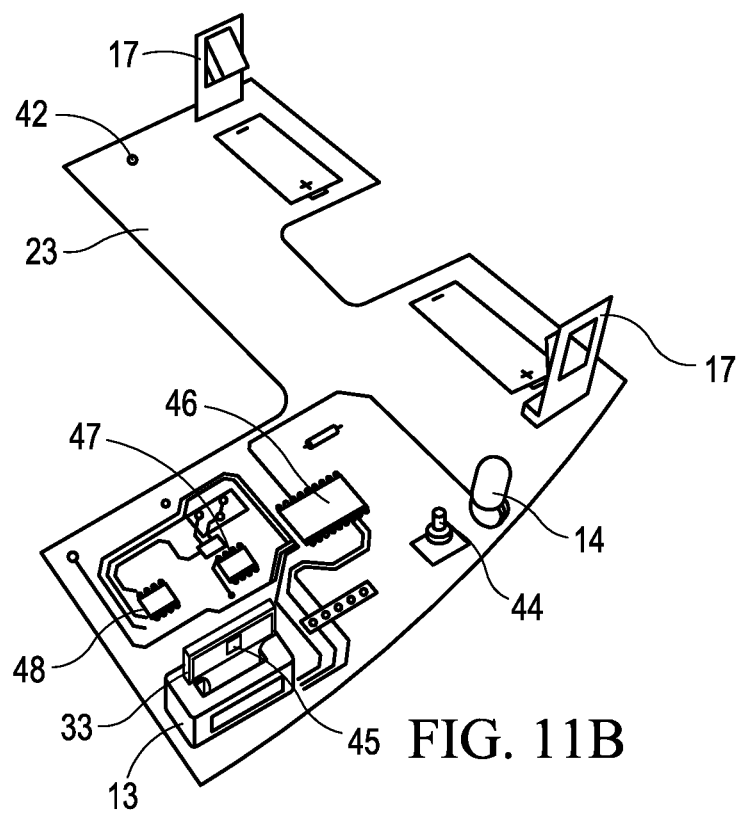

FIGS. 11A and 11B are perspective views of the main circuit board 23 and electronic key device 33 of the assembly of FIGS. 1-4. The printed circuit board comprising the electronic key device 33 consists of four contact surfaces 40 for interconnection to connector 13, and a read-only memory EEPROM 45. The EEPROM 45 contains written code that can be detected by the microprocessor 46 mounted on the main control board 23.

Current to the electrochemical generator is controlled by means of current controller 47, in cooperation with digital potentiometer [e.g. MCP 4001] 48, which has two control lines that allow the microprocessor 46 to set the resistance and thereby the current. A single multi-purpose push-button switch 44 and LED 41 are used to set currents and to provide user with information about status of fluid delivery from the reservoir.

Operation of the Fragrance Releaser

The liquid-filled refill sub-assembly 97, including the fluid receiving pad 7, is held by its two wings 27A, 27B, 28 (guided by the four guides on the base plate) and inserted simultaneously into the gas generator holder and the two base plate slots 12, one of which allows the four contact surfaces of the electronic key device 33 to mate with the connector 13 located on the main PCB. In this arrangement, the refill 97 is now securely located and held into its operating position. The fluid receiving pad 7 is securely held in place wrapped around the refill shoulder elements 10 and anchored by the prongs 9 located on both shells.

As a precautionary measure, to prevent operating the dispenser 99 without an open fluid exit port, the exit port is fitted with a "break-away" snap arm element 90. The fill port opening 38 size is adequate to match the filling equipment's size requirements.

Once filled, the reservoir 6 is sealed-off by means of a snap arm element 90. The solid arm 36 includes a hollow port opening 38 that matches the geometry of the fill port 8. The arm element 90 is bonded to the fill port spike 34. The fluid exit opening 38 is smaller than the fill port 8A to prevent liquid "puddling" and to increase the linear displacement rate of the exiting fluid, which is eventually captured by the fluid absorbent pad 7 from which it can evaporate.

The purpose of the arm 36 is to prevent closure of the dispenser lid 2 prior to opening the exit port, an event that could occur through inattention. The presence of the arm 36 prevents such an event. However, by snapping the lever arm 36 at the break point 37, the arm 36 can be removed (and the fluid exit opening 38 is then open). The system is now ready to start.

Starting the dispenser 99 is achieved by connecting the gas generator 18 to the power source (i.e. batteries 4). Through this action, the electrochemical cell module (ECM) 18 is activated, thereby controllably generating oxygen gas as a result of the following reactions:

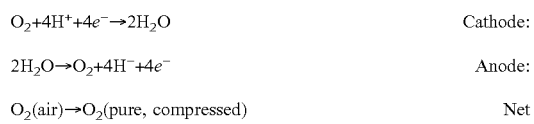

The generated oxygen is released from the anode and into the module sleeve 39, after which it then travels to the gas chamber 93 gas-side shell 26 via the gas inlet nipple 29. As gas continues to enter the chamber 93, pressure (via the internal diaphragm 95) is applied to the liquid in the liquid chamber 94 of the liquid-side shell 25, resulting in the liquid leaving the fluid exit port 8, where it is discharged onto the pad 7 from which it can evaporate.

Other gas sources can be used with the dispenser assembly 99 of the present invention. As described in Maget; U.S. Pat. No. 7,681,809, these gas sources are generally electrolytic devices (oxygen enrichment, water electrolysis, electrolytic decomposition of organic acids, Maget, U.S. Pat. No. 6,413,238) or gas cells described by Winsel, in U.S. Pat. No. 5,242,565.

Controlling the Dispenser

Controlling the operation of the releaser 99 can be achieved by means as simple as a resistor, or alternatively, by more complex means. For two-part dispensers, where the (semi)permanent part is re-usable multiple times for time periods of years, the cost of the electronics-per-use can be rather low and therefore more complex functions are possible since the life of the electrochemical cell module is years, the system life is dependent on the power source energy storage capacity (expressed in mAhr), since operating voltages of the cell 18 are less than the nominal voltage of 1.5 volts. For example, for a fluid delivery rate of 1 mL/day, the theoretical current of the cell module is 181 microamps, which translates into the dispenser 99 consuming 4.35 mAhr for every mL of fluid dispensed. One C-size battery with a capacity of about 8,000 mAhr could therefore deliver up to 1,800 mL of fluid. For a reservoir volume of 90 mL, this quantity corresponds to 20 uses per battery charge. Each use would last up to 3 months for a total available usage period of 5 years for one C-size battery. However, 2 series-connected batteries are required to achieve the voltage required to operate the electronic circuit.

The following will describe one electronic sub-assembly aimed at achieving specific functions. Obviously many others are possible. In order to fully capitalize on such an energy-efficient gas generator 18, the control electronics must also be energy-efficient in order to optimize the cost-per-release.

The circuit is turned ON by pressing and then releasing the push-button 44. If the anti-theft key device 33 is properly installed in the connector 13, and the processor deems that the refill 97 is legal and not empty, the circuit powers up and lights the LED 14 for two seconds. After a one second delay the current is enabled at the same current level at which it was previous to shut-down (the processor has its own non-volatile memory to store this information, separate from the non-volatile memory in the key). The LED 14 then blinks a certain number of times to indicate the current level. For example, the LED will blink once for X microamps, twice for Y microamps and three times for Z microamps. To change the current setting, the user quickly presses and releases the push-button. This advances the current through the three settings and goes back to the sequence XYZ, XYZ, etc. If the pushbutton is held depressed for too long of a time, the circuit will shuts off. When the processor estimates that the refill is empty, based on the selected current settings, the LED 14 will blink four times, the processor writes the value to the electronic key 33 that indicates that the device is empty, and then the circuit shuts down.

If the key 33 is not inserted when a circuit start is attempted, the processor will detect the condition, will cause the LED to blink five times, and then the circuit shuts down. Also if the key is removed while the circuit is running, the LED blinks four times and the circuit shuts down. If a key 33 is inserted that has an empty code stored, the processor will detect this condition, will cause the LED to blink six times, after which the circuit will shut off.

Performance of the Dispenser

Figure 12:
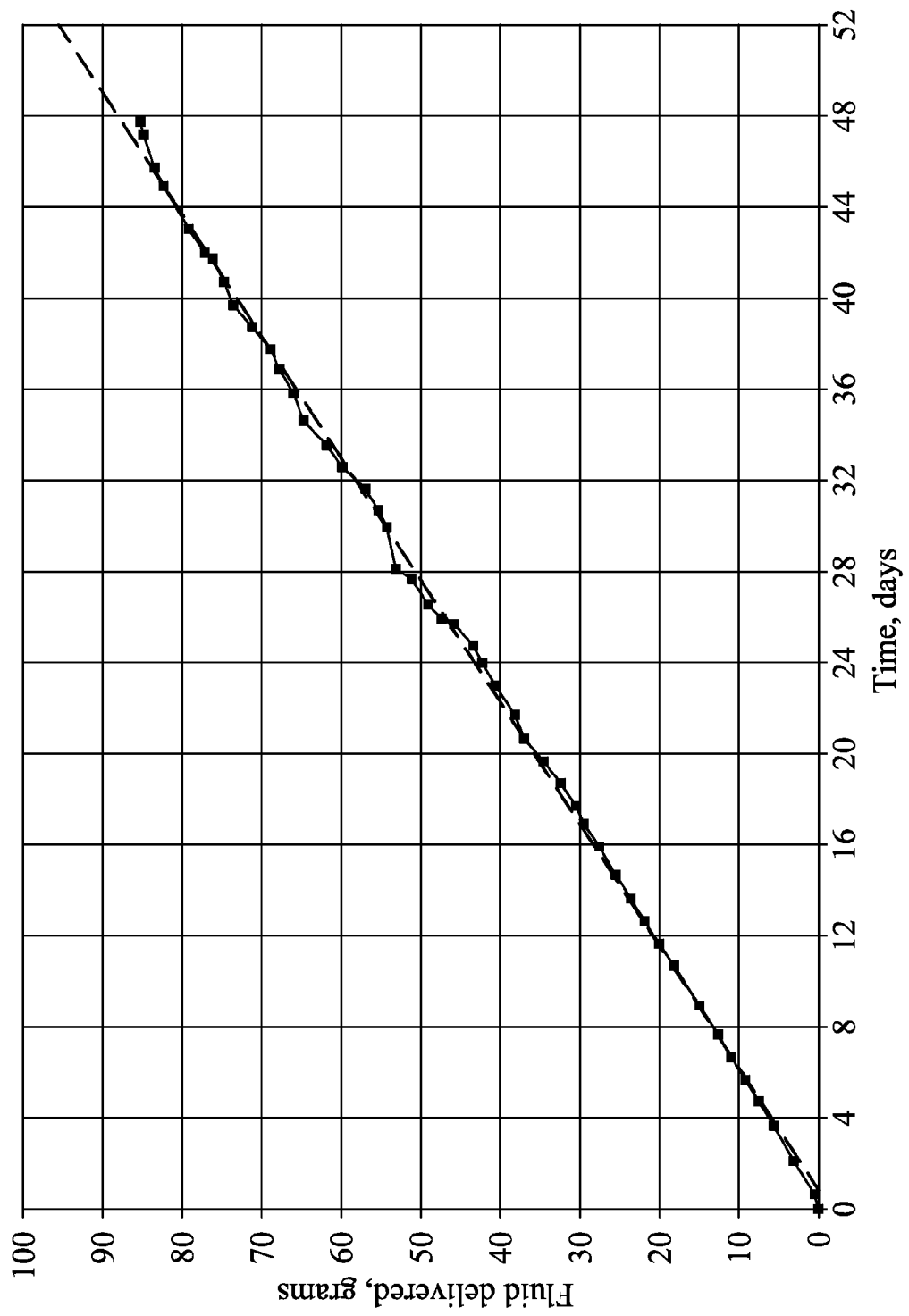
FIG. 12 is a chart depicting exemplary fluid delivery results of the assembly of the present invention.

The fluid delivery profile for water delivered from a reservoir with a shell area of 80 cm$^2$, a fill volume of 88 mL, a diaphragm of 100 microns thick Barex, operating at a current of 400 microamps, is illustrated in FIG. 12. The average fluid delivery rate over a period of 45 days is 1.88 mL/day. The theoretical flow rate at that current is 2.21 mL/day. Therefore the system efficiency is about 85%, with the lost efficient being caused mainly by the pressure required to move the diaphragm across the reservoir 6.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

| Index of Parts |
| --- |
| 1 Base plate |
| 2 Lid |
| 3 Air slots |
| 4 Batteries |
| 5 Guides |
| 6 Reservoir |
| 7 Pad |
| 8 Fluid exit nozzle |
| 9 Prongs |
| 10 Shoulder elements |
| 11 Gas generator port |
| 12 Refill wing slots |
| 13 Key connector |
| 14 LED |
| 15 Switch |
| 16 Wall-mount apertures |
| 18 Gas generator/ECM |
| 19 Air intake port |
| 20 Module seal |
| 23 Main PCB |
| 24 Cathode and anode terminals |
| 25 Liquid-side shell |
| 26 Gas side shell |
| 27A Liquid side shell wings |
| 27B Gas side shell wings |
| 28 Modified wing |
| 29 Nipple |
| 31 Flange |
| 32 Stiffening members |
| 33 Electronic key device |
| 34 Fill port spike |
| 35 Fill port flange |
| 36 Break-away arm |
| 37 Breakaway surface |
| 38 Fluid exit opening |
| 39 Gas module sleeve |
| 40 4-pin connector |
| 41 Mounting screw slots |
| 42 Apertures for back plate attachment |
| 43 Battery terminals |
| 44 Push button |
| 45 EEPROM |
| 46 Microprocessor |
| 47 Current controller |
| 48 Digital potentiometer |
| 49 Anode lead channel |
| 50 Cathode lead channel |
| 51 Screw ports (2) |
| 52 ECM seal |
| 53 Spring |
| 54 Spring lead (cathode) |
| 55 Washer |
| 56 Washer lead (anode) |
| 57 Screws (2) to base plate |
| 58 Screws for compression plate |
| 59 Compression plate |
| 60 ECM cavity |
| 88 Break-away arm element head portion |
| 89 ECM module housing |
| 90 Break-away arm element |
| 91 Fill port element interior opening |
| 92 Fill port element module |
| 93 Gas chamber |
| 94 Liquid chamber |
| 95 Diaphragm |
| 96 Fingers |
| 97 Refill module assembly |
| 98 Gas generator module assembly |
| 99 Two-part, wall-mountable electrochemical dispenser assembly |

What is claimed is:

1. A liquid emitter combination comprising:
 a reusable gas generator subassembly for generating gaseous material;
 a disposable liquid emitter subassembly associated with said gas generator such that emission of said gaseous material by said gas generator subassembly will cause said disposable liquid emitter subassembly to emit liquid contained within a liquid chamber formed therein, said disposable liquid emitter subassembly comprising a housing separated into two individual chambers by a pliable sheet passing therethrough, wherein one said individual chamber is said liquid chamber; and
 an absorbant pad wrapped about a portion of said disposable liquid emitter subassembly whereby said pad is in spaced relation to outer walls defining said housing.

2. The combination of claim 1, wherein the other of said two individual chambers is a gas chamber, said gas chamber being in fluid communication with said reusable gas generator subassembly.

3. The combination of claim 2, wherein said disposable liquid emitter subassembly housing further comprises:
 a plurality of outwardly-facing prongs dispersed about the outside of said housing; and
 said absorbant pad is attached to said prongs.

4. The combination of claim 3, wherein said housing of said disposable liquid emitter subassembly defines a perimeter edge between said two individual chambers, and said liquid emitter subassembly further comprises:
 a fluid exit port element extending from said perimeter edge, said fluid exit port element defining an internal bore in fluid communication with said liquid chamber; and
 wherein said gas chamber is not in fluid communication with said fluid exit port.

5. The combination of claim 4, further comprising a gas intake nipple element extending from one of said outer walls of said housing, said gas intake nipple defining an internal bore formed therethrough, said internal bore of said gas intake nipple in fluid communication with said gas chamber and said reusable gas generator subassembly.

6. The combination of claim 5, further comprising:
 a key receptacle located within said reusable gas generator subassembly;
 a key device located within said disposable liquid emitter subassembly; and
 whereby when said liquid emitter subassembly is combined with said gas generator subassembly, said key device will mate with said key receptacle such that information stored on said key device is accessible to said gas generator subassembly.

7. The combination of claim 6, wherein said liquid emitter subassembly housing is formed in a flattened disc shape having said gas intake nipple extending from said gas chamber in a direction that is generally perpendicular to the direction that said fluid exit port extends from said housing.

8. The combination of claim 7, wherein said absorbant pad defines an aperture formed therethrough, and through which said gas intake nipple protrudes when said absorbant pad is attached to said prongs.

9. The combination of claim 8, further comprising a second said liquid emitter subassembly further comprising a break-away element attached to a distal end defined by said fluid exit port element of said second liquid emitter subassembly, said break-away element creating a liquid-tight seal of said fluid exit port internal bore, whereby said second said liquid emitter subassembly being exchangeable with said disposable liquid emitter subassembly after said disposable liquid emitter subassembly is disposed of.

10. An evaporative dispenser device, comprising:
 a reusable gas generator subassembly for generating gaseous material; and
 a disposable liquid emitter subassembly associated with said gas generator such that emission of said gaseous material by said gas generator subassembly will cause said disposable liquid emitter subassembly to emit liquid onto an absorbent pad for evaporation into the environment surrounding said dispenser device, said liquid contained within a liquid chamber formed within said liquid emitter subassembly, said disposable liquid emitter subassembly comprising a housing separated into two individual chambers by a pliable sheet passing therethrough, one said individual chamber being said liquid chamber, said housing further comprising a plurality of prongs extending therefrom to which said absorbant pad is attached, whereby said absorbant pad is in spaced relation to outer walls of said housing.

* * * * *